US00PP34382P2

(12) United States Plant Patent
Matsumoto

(10) Patent No.: US PP34,382 P2
(45) Date of Patent: Jun. 28, 2022

(54) ***VERBENA* PLANT NAMED 'WNVECPPK'**

(50) Latin Name: *Verbena rigida*
Varietal Denomination: WNVECPPK

(71) Applicant: Rika Matsumoto, Omihachiman (JP)

(72) Inventor: Rika Matsumoto, Omihachiman (JP)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/371,695

(22) Filed: Jul. 9, 2021

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Annette H Para
(74) *Attorney, Agent, or Firm* — C. Anne Whealy

(57) ABSTRACT

A new and distinct cultivar of *Verbena* plant named 'WNVECPPK', characterized by its initially upright to outwardly spreading plant habit; vigorous growth habit and rapid growth rate; freely branching habit; dark green-colored leaves; early and freely flowering habit; rounded inflorescences with purplish pink-colored flowers that are held above and beyond the foliar plane; and good garden performance and high temperature tolerance.

2 Drawing Sheets

Figure 1:
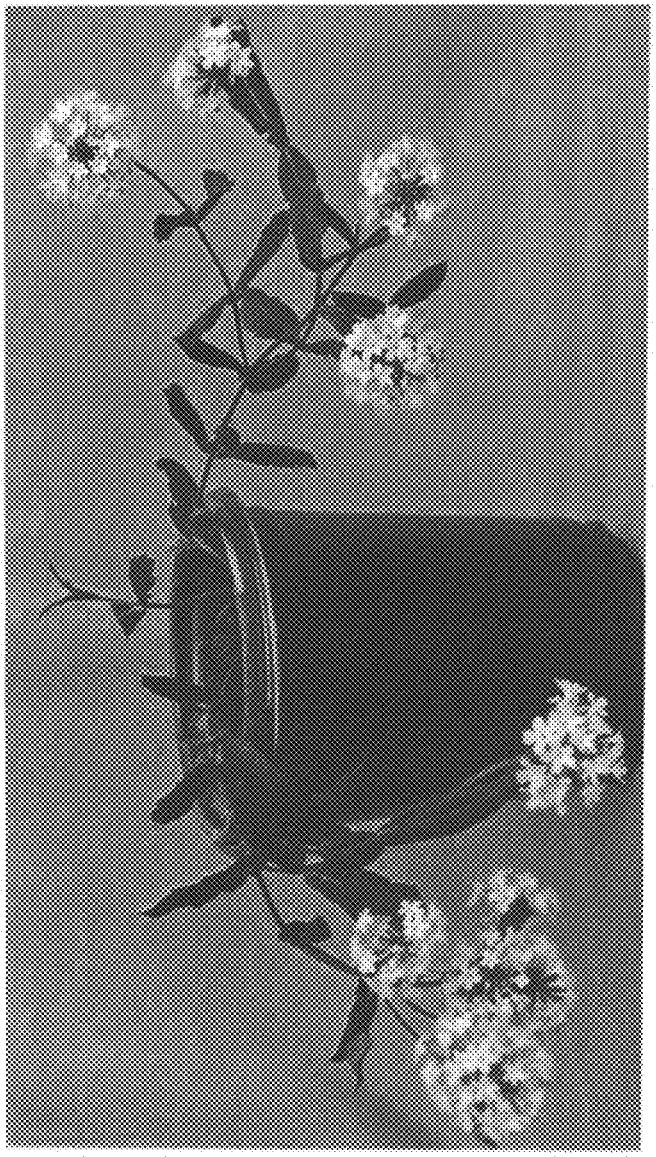

Botanical designation: *Verbena rigida.*
Cultivar denomination: 'WNVECPPK'.

CROSS-REFERENCED TO CLOSELY-RELATED APPLICATIONS

Title: *Verbena* Plant Named 'WNVECPPUR'
Inventor/Applicant: Rika Matsumoto
Plant patent application Ser. No. 17/371,744

BACKGROUND OF THE INVENTION

The present invention relates to a new and distinct cultivar of *Verbena* plant, botanically known as *Verbena rigida*, commonly referred to as Tuberous *Verbena* and hereinafter referred to by the name 'WNVECPPK'.

The new *Verbena* plant is a product of a planned breeding program conducted by the Inventor in Higashiomi Shiga, Japan and Bonsall, Calif. The objective of the breeding program is to create new *Verbena rigida* plants with improved plant habit and new and unique flower colors.

The new *Verbena* plant originated from a cross-pollination made by the Inventor on May 23, 2016 in Higashiomi Shiga, Japan of a proprietary seedling selection of *Verbena rigida* identified as code number 09V985-01, not patented, as the female, or seed, parent with *Verbena rigida* 'Polaris', not patented, as the male, or pollen, parent. The new *Verbena* plant was discovered and selected by the Inventor as a single flowering plant from within the progeny of the stated cross-pollination in a controlled greenhouse environment in Bonsall, Calif. on May 26, 2017.

Asexual reproduction of the new *Verbena* plant by vegetative terminal cuttings in a controlled environment in Bonsall, Calif. since May 29, 2017, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNVECPPK'. These characteristics in combination distinguish 'WNVECPPK' as a new and distinct *Verbena* plant:

1. Initially upright to outwardly spreading plant habit.
2. Vigorous growth habit and rapid growth rate.
3. Freely branching habit.
4. Dark green-colored leaves.
5. Early and freely flowering habit.
6. Rounded inflorescences with purplish pink-colored flowers that are held above and beyond the foliar plane.
7. Good garden performance and high temperature tolerance.

Plants of the new *Verbena* can be compared to plants of the female parent selection. Plants of the new *Verbena* differ primarily from plants of the female parent selection in the following characteristics:

1. Plants of the new *Verbena* are more compact than and not as vigorous as plants of the female parent selection.
2. Plants of the new *Verbena* are more outwardly spreading than and not as upright as plants of the female parent selection.
3. Plants of the new *Verbena* have purplish pink-colored flowers whereas plants of the female parent selection have purple-colored flowers.

Plants of the new *Verbena* can be compared to plants of the male parent, 'Polaris'. Plants of the new *Verbena* differ primarily from plants of 'Polaris' in the following characteristics:

1. Plants of the new *Verbena* have larger flowers than plants of 'Polaris'.
2. Plants of the new *Verbena* have purplish pink-colored flowers whereas plants of 'Polaris' have pale lilac-colored flowers.

Plants of the new *Verbena* can be compared to plants of the *Verbena rigida* 'WNVECPPUR', disclosed in a U.S. Plant Patent application filed concurrently. In side-by-side comparisons, plants of the new *Verbena* differ primarily from plants of 'WNVECPPUR' in flower color as plants of the new *Verbena* have purplish pink-colored flowers whereas plants of 'WNVECPPUR' have violet-colored flowers.

Plants of the new *Verbena* can be compared to plants of the *Verbena rigida* 'Santos Purple', not patented. In side-by-side comparisons, plants of the new *Verbena* differ primarily from plants of 'Santos Purple' in the following characteristics:

1. Plants of the new *Verbena* are more compact than plants of 'Santos Purple'.
2. Plants of the new *Verbena* are more spreading than and not as upright as plants of 'Santos Purple'.
3. Plants of the new *Verbena* have more flexible stems than plants of 'Santos Purple'.
4. Plants of the new *Verbena* have purplish pink-colored flowers whereas plants of 'Santos Purple' have deep purple-colored flowers.

Plants of the new *Verbena* can also be compared to plants of the *Verbena bonariensis* X *Verbena hybrida* 'INVEBPUTOW', disclosed in U.S. Plant Pat. No. 27,722. In side-by-side comparisons, plants of the new *Verbena* differ primarily from plants of 'INVEBPUTOW' in the following characteristics:

1. Plants of the new *Verbena* are more spreading than and not as upright as plants of 'INVEBPUTOW'.
2. Plants of the new *Verbena* have more flexible stems than plants of 'INVEBPUTOW'.
3. Plants of the new *Verbena* have purplish pink-colored flowers whereas plants of 'INVEBPUTOW' have purple violet-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'WNVECPPK' grown in a container.

Figure 2:
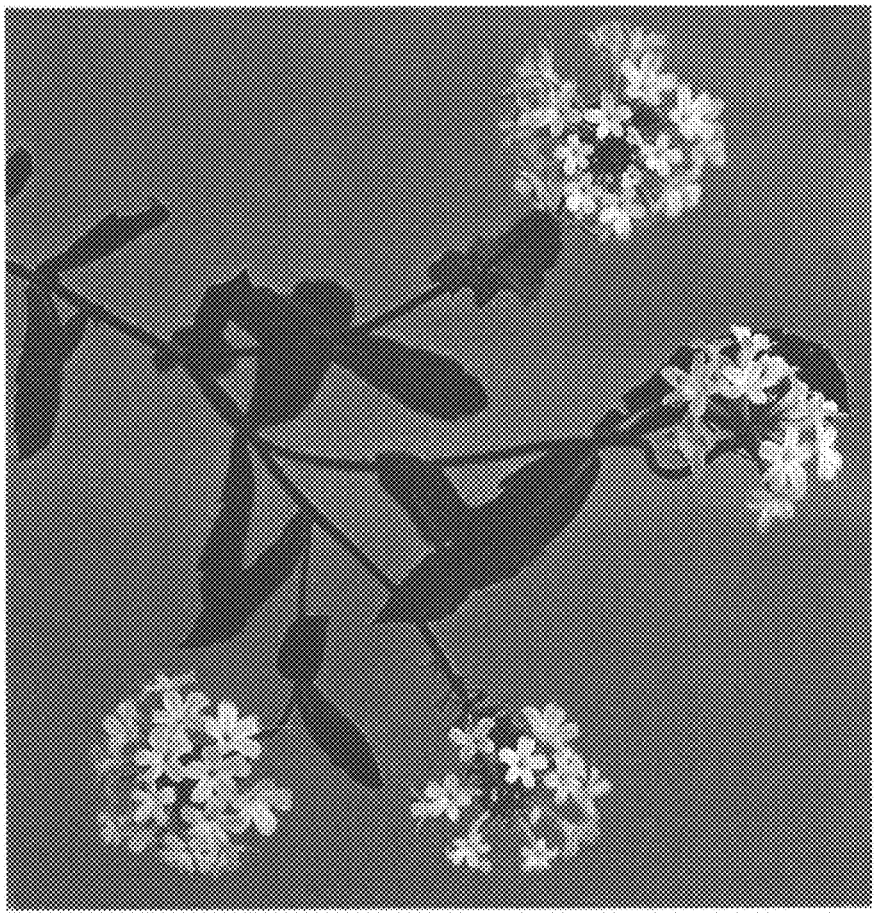

The photograph on the second sheet (FIG. 2) is a close-up view of a typical flowering plant of 'WNVECPPK'.

DETAILED BOTANICAL DESCRIPTION

The aforementioned photographs and following observations and measurements describe plants grown during the late summer and early autumn in 10.8-cm containers in a corrugated polycarbonate-covered greenhouse in Carlton, Mich. and under cultural practices typical of commercial *Verbena* production. During the production of the plants, day temperatures averaged 26° C., night temperatures averaged 20° C. and light levels averaged 9,290 foot-candles. Plants were pinched three weeks after planting and were twelve weeks from planting rooted cuttings when the photographs and description were taken. In the following description, color references are made to The Royal Horticultural Society Colour Chart, 2015 Edition, except where general terms of ordinary dictionary significance are used.

Botanical classification: *Verbena rigida* 'WNVECPPK'.

Parentage:

*Female, or seed, parent.*—Proprietary seedling selection of *Verbena rigida* identified as code number 09V985-01, not patented.

*Male, or pollen, parent.*—*Verbena rigida* 'Polaris', not patented.

Propagation:

*Type cutting.*—Vegetative terminal cuttings.

*Time to initiate roots, summer.*—About three days at temperatures ranging from about 16° C. to 29° C.

*Time to initiate roots, winter.*—About four days at temperatures ranging from about 16° C. to 29° C.

*Time to produce a rooted plant, summer.*—About 15 days at temperatures ranging from about 16° C. to 29° C.

*Time to produce a rooted plant, winter.*—About 20 days at temperatures ranging from about 16° C. to 29° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Initially upright to outwardly spreading plant habit; freely branching habit with lateral branches potentially developing at every node, pinching enhances branching potential; vigorous growth habit and rapid growth rate.

*Plant height.*—About 9 cm.

*Plant diameter (spread).*—About 35 cm.

Lateral branch description:

*Length.*—About 27 cm.

*Diameter.*—About 2.5 mm to 3 mm.

*Internode length.*—About 3.5 cm to 4.75 cm.

*Orientation.*—Initially upright then outwardly spreading; horizontal to downward.

*Strength.*—Strong; flexible.

*Texture and luster.*—Densely pubescent; pubescence is short, fine and rough; slightly glossy; becoming woody with subsequent development.

*Color, developing.*—Close to 146A.

*Color, developed.*—Close to 147A variably tinged with close to 187A; if woody, close to 199A.

Leaf description:

*Arrangement.*—Opposite, simple; sessile.

*Length.*—About 4.75 cm to 5.5 cm.

*Width.*—About 1.5 cm to 1.75 cm.

*Shape.*—Oblong.

*Apex.*—Acuminate.

*Base.*—Cuneate.

*Margin.*—Irregularly serrate.

*Texture and luster, upper and lower surfaces.*—Moderately pubescent, rough; coriaceous; slightly rugose; matte.

*Venation pattern.*—Pinnate.

*Color.*—Developing leaves, upper surface: Close to 147A. Developing leaves, lower surface: Darker green than 146A. Fully expanded leaves, upper surface: Close to 139A; venation, proximally, close to 144A and distally, close to 139A. Fully expanded leaves, lower surface: Darker green than 146A; venation, close to 146A.

Flower description:

*Flower arrangement and habit*.—Sessile salverform flowers arranged in rounded to almost spherical terminal cymes with two to three inflorescences per terminal; flowers face upward or outwardly depending on the position in the inflorescence; freely flowering habit with about 15 to 20 open flowers at one time per inflorescence and about 70 to 75 flowers developing per inflorescence; numerous inflorescences develop per plant during the flowering season.

*Natural flowering season*.—Plants flower continuously from spring until the autumn; early flowering habit, plants begin flowering about five to six weeks after planting.

*Flower longevity*.—Flowers last about five to seven days on the plant; flowers not persistent.

*Fragrance*.—None detected.

*Inflorescence height*.—About 3.5 cm.

*Inflorescence diameter*.—About 3.75 cm.

*Flower buds*.—Length: About 7.5 mm. Diameter: About 2.5 mm. Shape: Oblong. Texture and luster: Densely pubescent; slightly glossy. Color: Close to 146A slightly and variably tinged with close to 187A.

*Flower diameter*.—About 1 cm.

*Flower depth* (*height*).—About 1.1 cm.

*Throat diameter*.—About 1 mm.

*Tube length*.—About 9 mm.

*Tube diameter, proximally*.—About 1.5 mm.

*Corolla*.—Arrangement: Single whorl of five fused petals fused towards the base into a slender narrow tube. Petal lobe length: About 4.5 mm. Petal lobe width: About 3.5 mm. Petal lobe shape: Oblong. Petal lobe apex: Obtuse to retuse. Petal margin: Entire; not undulate. Petal texture and luster, upper and lower surfaces: Smooth, glabrous; matte. Throat texture and luster: Moderately pubescent; matte. Tube texture and luster: Densely pubescent; matte. Color: Petal lobes, when opening, upper surface: Close to 62B. Petal lobes, when opening, lower surface: Close to 62C. Petal lobes, fully opened, upper surface: Close to 62A; towards the margins, close to 62B; towards the throat, close to 62A; venation, similar to lamina colors; colors becoming closer to 62C with subsequent development. Petal lobes, fully opened, lower surface: Close to 62C; venation, close to 62C; color becoming closer to 62D with subsequent development. Throat: Distally, close to 62C and proximally, close to 64A; venation, similar to lamina colors. Tube: Close to 64A; venation, close to 64A.

*Calyx*.—Arrangement: Single whorl of five fused sepals fused towards the base into a slender tube. Length: About 5 mm. Diameter: About 2.5 mm. Sepal length: About 5 mm. Sepal width: About 1 mm. Sepal shape: Acicular. Sepal apex: Acuminate. Sepal margin: Entire. Sepal texture and luster, upper surface: Pubescent; moderately glossy. Sepal texture and luster, lower surface: Pubescent; slightly glossy. Sepal color: When opening, upper surface: Close to 146A. When opening, lower surface: Close to 146A tinged with close to 187A. Fully opened, upper and lower surfaces: Close to 146A.

*Peduncles*.—Length: About 2.5 cm. Diameter: About 1 mm. Strength: Strong; flexible, wiry. Aspect: Upright to 45° from stem axis. Texture and luster: Densely pubescent; rough; slightly glossy. Color: Close to 144A.

*Reproductive organs*.—Stamens: Quantity and arrangement: Five per flower, filaments partially adnate to corolla tube. Filament length: About 3 mm. Filament color: Close to 144A. Anther size: About 0.5 mm by 1 mm. Anther shape: Oblong. Anther color: Close to 144A. Pollen amount: None observed. Pistils: Quantity: One per flower. Pistil length: About 2 mm. Style length: About 1.75 mm. Style color: Close to 144A. Stigma shape: Rounded. Stigma diameter: Less than 1 mm. Stigma color: Close to 144A. Ovary color: Close to 144A. Fruits and seeds: To date, fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8a to 11b.

Pathogen & pest resistance: To date, plants of the new *Verbena* have not been observed to be resistant to pathogens and pests common to *Verbena* plants.

It is claimed:

1. A new and distinct *Verbena* plant named 'WNVECPPK' as illustrated and described.

* * * * *